United States Patent [19]

Palmer

[11] Patent Number: 5,571,084

[45] Date of Patent: Nov. 5, 1996

[54] MICROPROCESSOR-CONTROLLED VESTED LACTATION SYSTEM

[75] Inventor: William R. Palmer, Melbourne, Fla.

[73] Assignee: Spread Spectrum Inc., Melbourne, Fla.

[21] Appl. No.: 353,824

[22] Filed: Dec. 12, 1994

[51] Int. Cl.[6] ................................................. A61M 1/06
[52] U.S. Cl. ................................................. 604/74; 601/14
[58] Field of Search ........................... 119/14.01–14.04, 119/14.08, 14.1, 14.14, 14.18, 14.43, 14.47, 14.48; 601/6, 14; 604/74–76

[56] References Cited

U.S. PATENT DOCUMENTS

| | | | |
|---|---|---|---|
| 949,414 | 2/1910 | Cunningham | 604/76 |
| 2,542,505 | 2/1951 | Gascoigne | 604/74 |
| 3,238,937 | 3/1966 | Stein | 604/74 X |
| 4,673,388 | 6/1987 | Schlensog et al. | 604/74 |
| 4,772,262 | 9/1988 | Grant et al. | 604/74 |
| 4,886,494 | 12/1989 | Morifuji | 604/74 |
| 4,964,851 | 10/1990 | Larsson | 604/74 |
| 5,007,899 | 4/1991 | Larsson | 604/74 |

Primary Examiner—Corrine M. McDermott
Assistant Examiner—N. Kent Gring
Attorney, Agent, or Firm—Charles E. Wands

[57] ABSTRACT

A human lactation system allowing hands free operation and full mobility during use. All required hardware is attached to a user worn vest. The vest is fully adjustable to accommodate a wide variety of sizes and shapes of users. A pair of breast cups are mounted within the vest to provide an interface between the breast and vacuum system. Vacuum quick connect fittings and quick release valves are attached to the breast cups for convenience and safety. A vacuum pump assembly is mounted in the front side of the vest and fluidly connected to the breast cups thereby providing vacuum to extract lactate from a breast. The vacuum magnitude and cycle frequency are controlled by a microprocessor contained within the keypad/controller assembly. The microprocessor controlled vacuum cycle closely mimics an infant's natural sucking frequency. The system is powered by a battery pack attached to the back side of the vest.

12 Claims, 7 Drawing Sheets

5,571,084

MICROPROCESSOR-CONTROLLED VESTED LACTATION SYSTEM

FIELD OF THE INVENTION

The present invention relates to the field of human lactation systems (breast pumps). More specifically, the present invention is directed at an improved lactation system that will allow the user greater mobility while operating the system and greater control of the breast pumping intensity.

BACKGROUND OF THE INVENTION

Previous lactation devices include manual pumps, hand held battery operated pumps and AC powered devices. Manual lactation pumps require the use of reciprocating hand motion. The breast cup is held in place with one hand and the pump is actuated with either the same hand or, in some applications, both hands. The manual lactation pump can only be used on one breast at a time. The vacuum cycle frequency is controlled by the frequency of pump actuations. The vacuum magnitude is controlled by both a vent setting and the amount of force imparted by the user to each pump stroke. The hand held battery operated pump is activated by an electric switch controlling a small battery operated vacuum pump. These systems can only be used on one breast at a time. The vacuum cycle frequency is manually controlled by the manual release of vacuum through a hand operated release valve. The vacuum magnitude is controlled by the amount of time the pump is activated in conjunction with the amount of time the release valve is left closed.

Heavier duty (120 VAC) lactation pumps are available that can be used on both breasts simultaneously. The vacuum magnitude is adjustable via a vacuum bypass setting. However, the cycle frequency is preset by the manufacturer. Due to the requirement of an AC power source, mobility is severely limited.

SUMMARY OF THE INVENTION

An object of the present invention is to overcome the above-mentioned limitations which provides a light weight, user worn, compact lactation system (breast pump). The system provides sufficient pumping to both breasts simultaneously giving the user a hands free operation.

According to preferred embodiments of the present invention, a microprocessor controlled vested lactation system is provided which includes breast cups, high volume vacuum pump head, direct drive electric motor, vacuum tubing system, rechargeable battery pack, and keypad with microprocessor vacuum controller disposed within a lightweight adjustable fabric vest.

The vest is the method by which all required vacuum, electrical and interface components are transported by the user as a single self contained unit. The vest is adjustable for various user heights and vertical breast/nipple positions by changing the attachment points of the shoulder straps and/or the vertical location of the collection bottle/breast cup assembly. The vest is adjustable for various user girths and breast sizes by changing the attachment points contained within the system. The breast cups are composed of a flexible inner annular ring, rigid outer shell, bellows connection, vacuum fitting with disconnect and vacuum release valve. The inner annular ring is connected along its outer diameter to the outer shell. The ring is placed against the breast with the nipple centered within the inner diameter of the ring. A vacuum line is connected to a fitting attached to the upper portion of each outer shell. The bellows connection is located at the bottom of the outer shell along the shell centerline. The breast cup assemblies are attached to the collection bottles by means of a flexible bellows. The collection bottle/breast cup assembly position is maintained by a support that is adjustably affixed to the vest. Vacuum is supplied to the breast cups by means of a system of flexible tubing connected to the battery operated vacuum pump. The vacuum pump is contained within a pocket formed on the front of the vest located at or about waist level and near the torso centerline. The battery pack is contained within a pocket formed on the back of the vest located beneath the shoulder blade area, above the waist line and along the torso centerline. The vacuum magnitude and cycle frequency are controlled by user input to the keypad containing the microprocessor vacuum control. The keypad/controller is attached to one side of the vest vertically positioned approximately to the user waistline.

In operation, the user will choose a timed duration and a particular level setting that is a combination of vacuum magnitude and cycle frequency that both approximate an infant's natural sucking pattern and allow user flexibility with respect to the intensity of the suction. The microprocessor controller allows the vacuum magnitude to be set to a variety of low, medium and high settings. As a non limiting example, the high vacuum magnitude setting corresponds to an on time of 1.75 seconds and an off time of 1.25 seconds. The medium vacuum magnitude setting corresponds to an on time of 1.25 seconds and an off time of 0.75 seconds. The low vacuum magnitude setting corresponds to an on time of 0.75 seconds and an off time of 0.50 seconds. The length of vacuum cycle may be set to three or seven minutes, or combinations thereof. Once a particular combination is chosen the system is activated and a vacuum is formed in the region between the flexible inner annular ring and breast interface and the outer shell. This vacuum draws lactate from the breast causing it to flow downward first into the outer shell then down through the bellows finally reaching the collection bottles.

Advantages of the present invention include greater mobility, fully self contained, compactness and lightweight. The invention is controlled by the user to operate on one or both breasts. Also, the user controls the vacuum magnitude and cycle frequency. Each breast cup contains a vacuum release valve for user safety in the event a quick release is necessary. The invention is battery operated, rechargeable and fully portable allowing hands free operation.

Other objects, advantages and novel features of the present invention will become apparent from the following detailed description of the invention when considered in conjunction with the accompanying drawings.

DETAILED DESCRIPTION

Figure 1A:
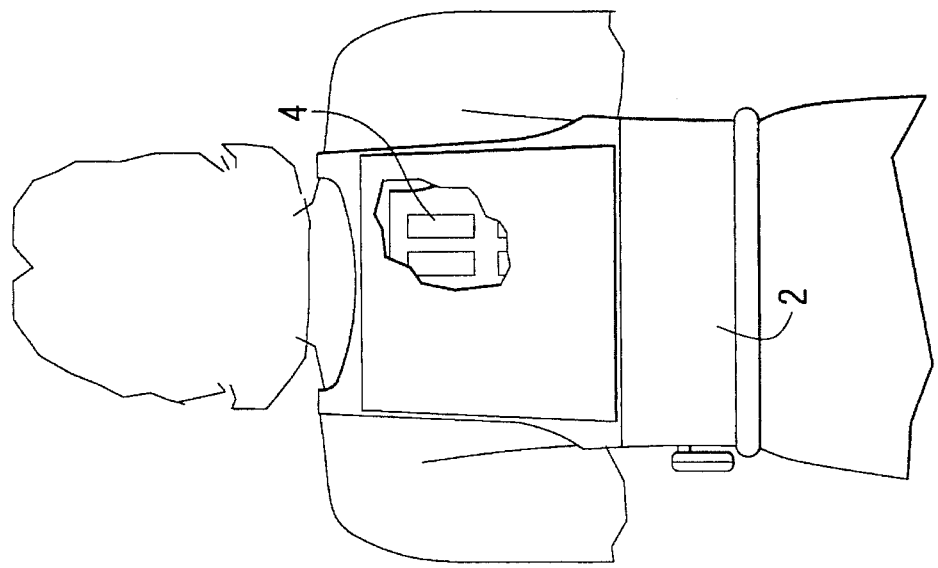
FIG. 1 is a schematic diagram of a microprocessor controlled vested lactation system as worn by the user.
Figure 1B:
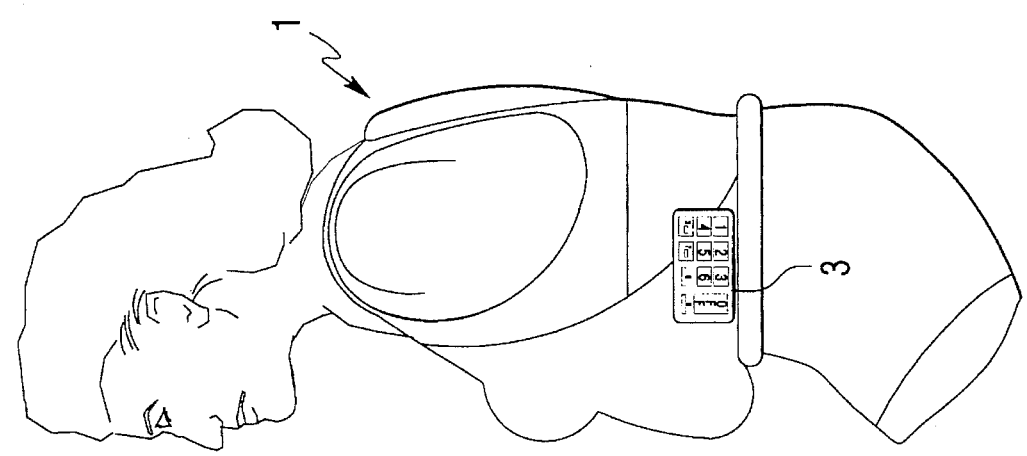
Figure 1C:
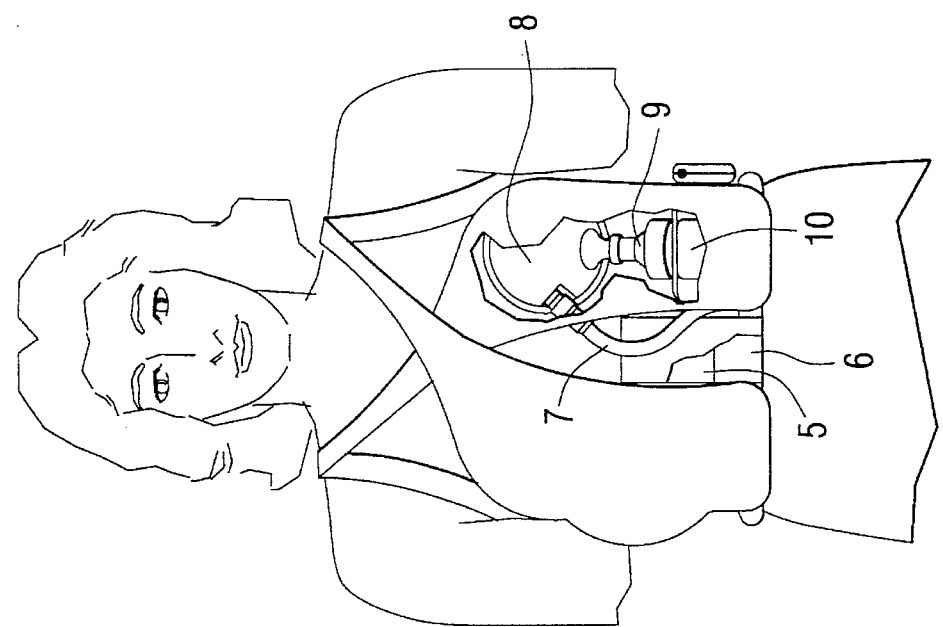
Figure 2C:
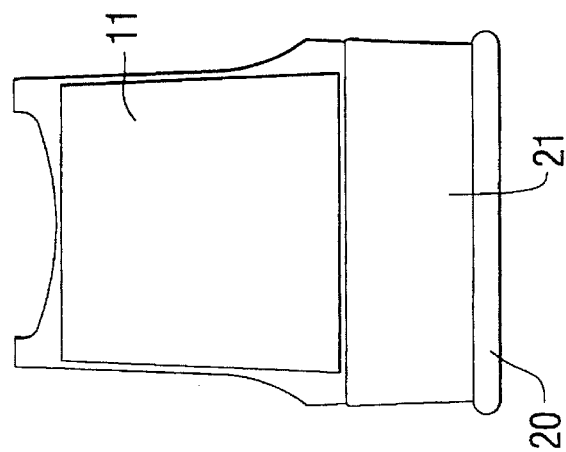
FIG. 2 is a detailed diagram of a vest for the vested lactation system of FIG. 1.
Figure 2B:
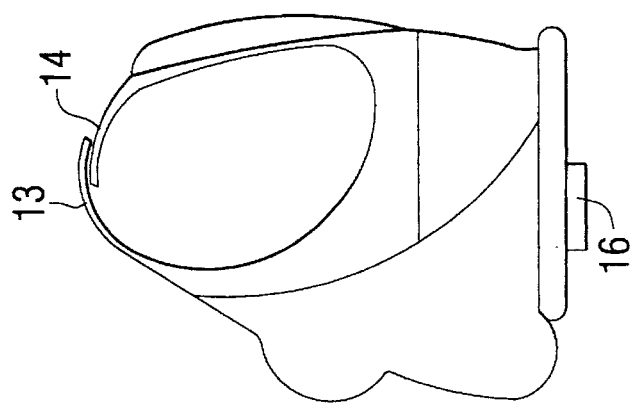
Figure 2A:
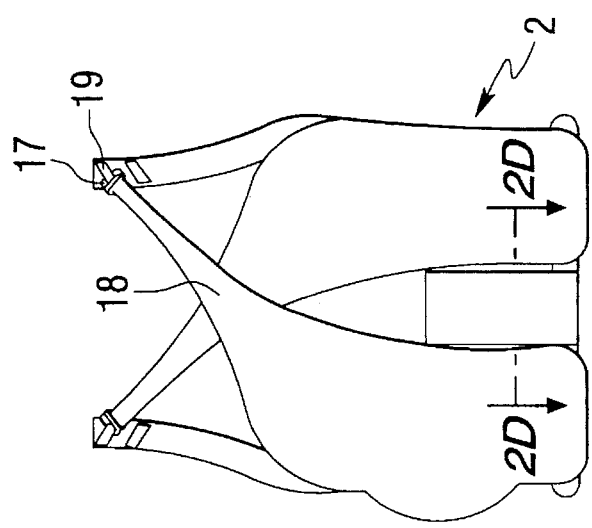
Figure 2D:
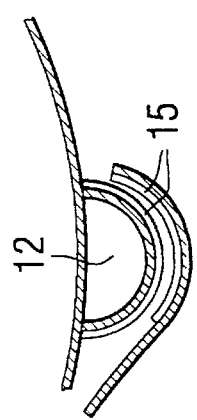
Figure 3C:
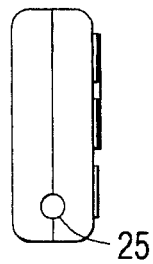
FIG. 3 is the physical layout of the controller for the vested lactation system of FIG. 1.
Figure 3A:
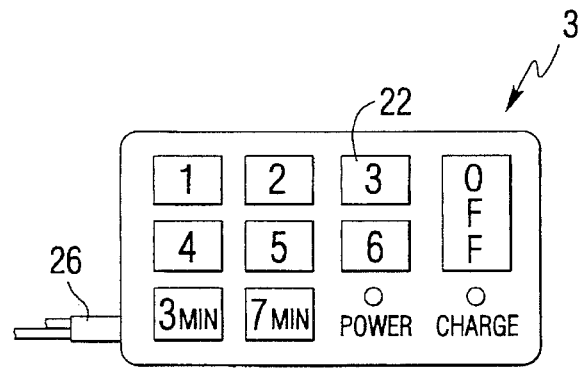
Figure 3B:
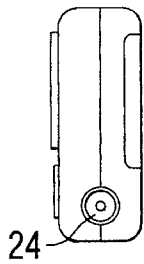
Figure 3D:
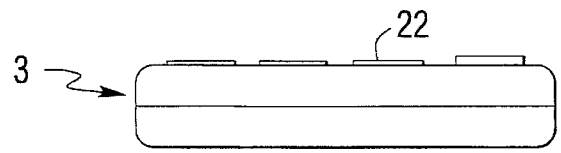
Figure 3E:
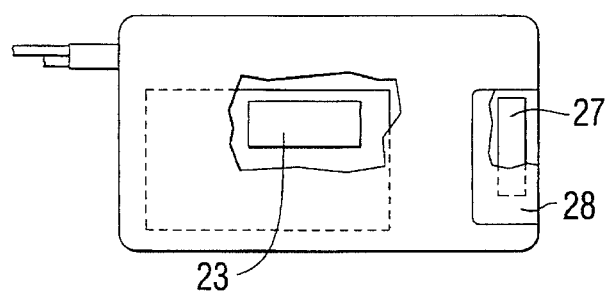

Referring to FIG. 1, a microprocessor controlled vested lactation system 1 comprises a vest 2, a controller 3, a battery pack 4, a direct drive motor 5, a high volume vacuum pump head 6, vacuum tubing 7, two breast cups 8, two bellows 9 and two collection bottles 10.

Referring to FIG. 2, incorporated into the vest 2 are pocket 11 for mounting battery pack 4 and pocket 12 for mounting motor 5 and pump head 6. The shoulder straps 13 and strap snaps 14 allow vertical adjustment of the system. The hook and loop fastener (Velcro) 15 at each end of the waist band allow circumferential adjustment of the system. The hook and loop fastener 16 at left side provides attachment of controller 3. The hook 17 at the end of the breast crossover flap 18 and the fabric loops 19 located on shoulder straps provide lateral support of the collection bottle/breast cup assembly. The fabric channel 20 at bottom of waist band 21 provides support for vacuum tubing 7.

Referring to FIG. 3, the controller 3 comprises a keypad 22 for user input, microprocessor 23, a power supply jack 24 for recharging the battery pack 4 (and wall power operation if batteries are not charged), wiring port 25 for connection to wiring harness 26, and a replaceable fuse 27 behind an access cover 28. The controller gives the user the ability to program the lactation cycles by choosing various settings of vacuum magnitude, cycle frequency and total lactation time.

Figure 4A:
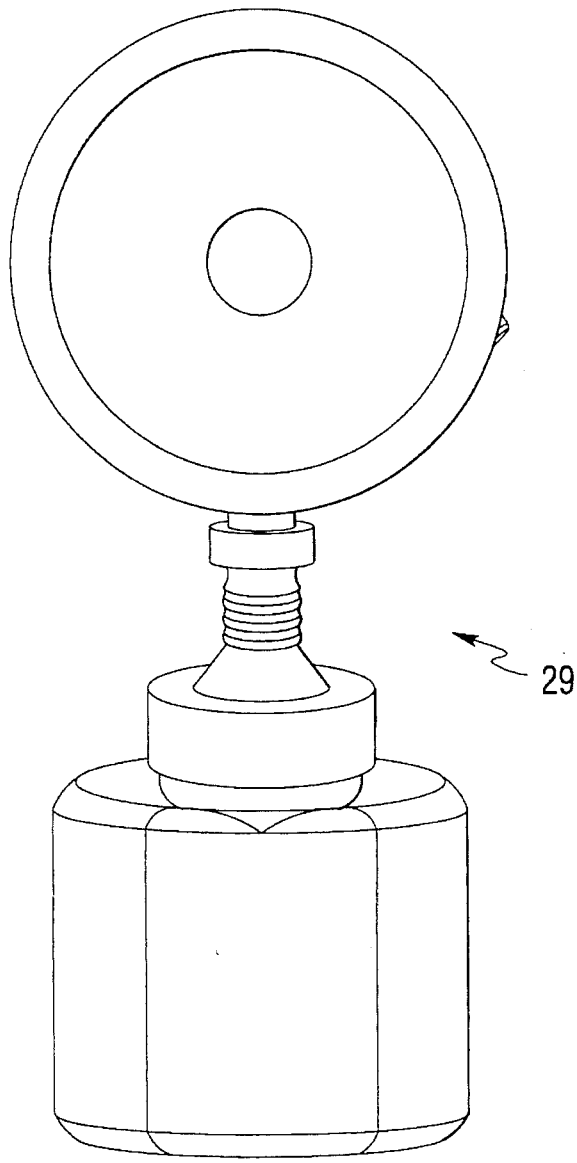
FIG. 4 is a detailed diagram of a collection bottle/breast cup assembly for the vested lactation system of FIG. 1.
Figure 4B:
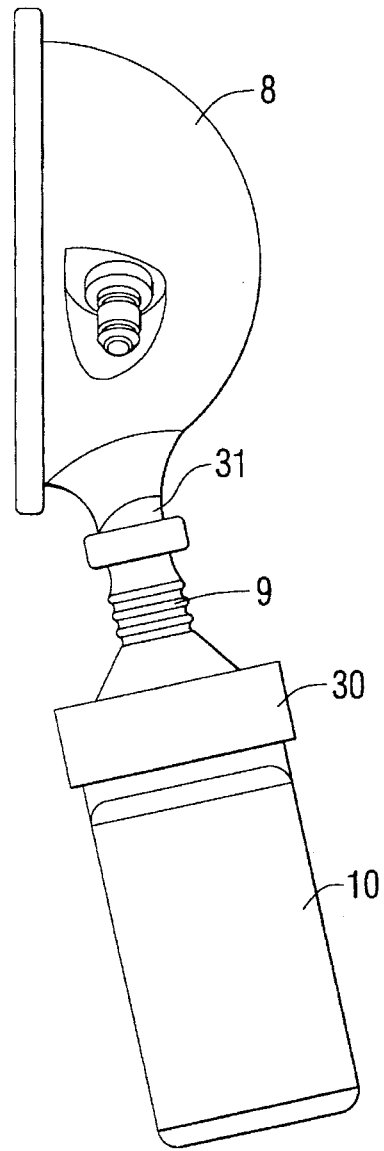

Referring to FIG. 4, the collection bottle/breast cup assembly 29 comprised of a flexible bellows 9 which is the interface device of the breast cup assembly 8 and collection bottle 10. The bellows 9 allows greater flexibility of the breast cup assembly 8 position in relation to the remainder of the system. The bellows 9 allows easy disassembly for cleaning. The bellows 9 is attached to the collection bottle 10 with a screw on bottle escutcheon 30 and is attached to breast cup drainage nipple 31 via a snap fit.

Figure 5B:
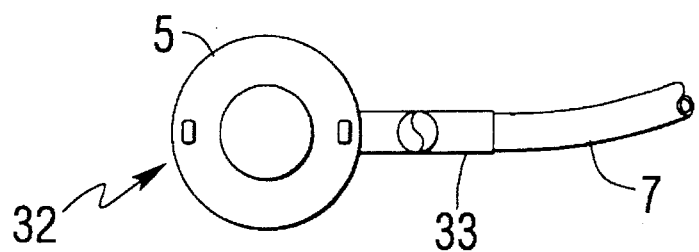
FIG. 5 is a diagram of the location of a vacuum pump assembly and routing of vacuum tubing for the vested lactation system of FIG. 1.
Figure 5A:
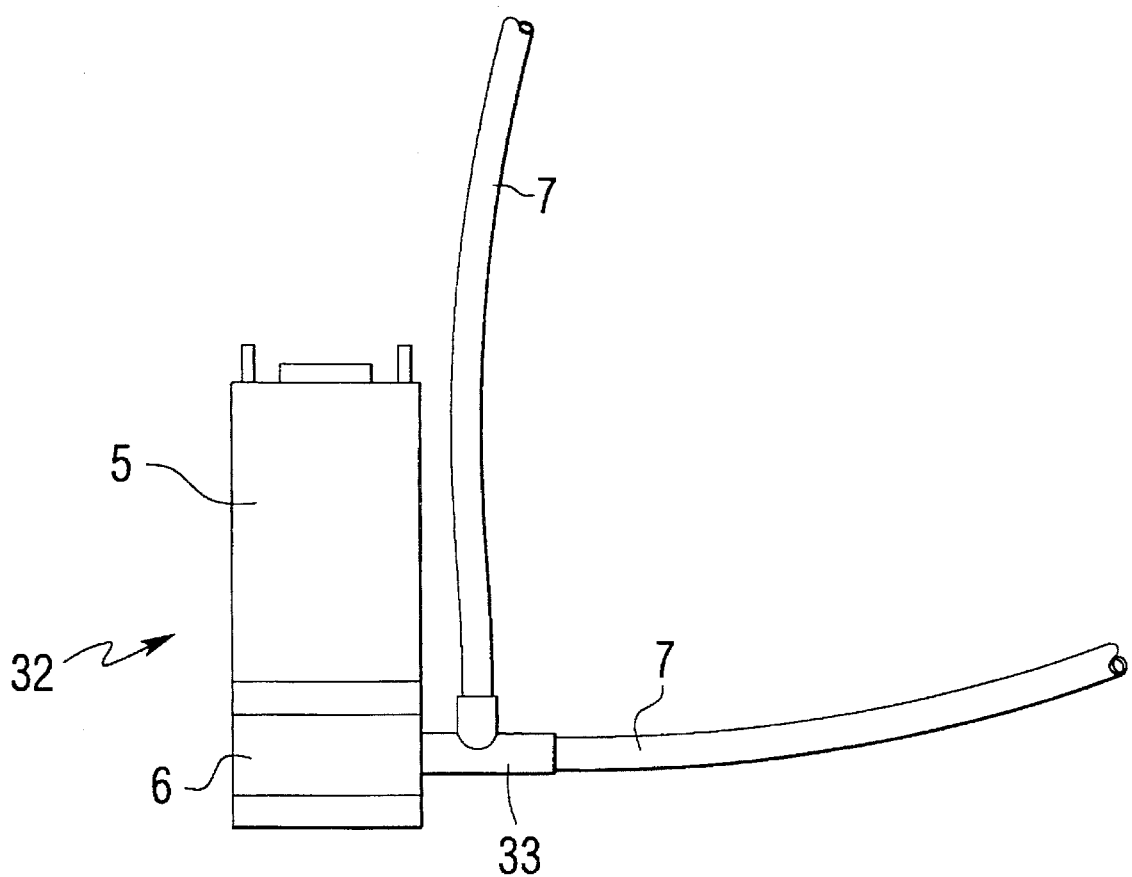

Referring to FIG. 5, the vacuum pump assembly 32, comprised of a direct drive motor 5 and a high volume vacuum pump head 6, and a vacuum line "T" fitting 33. The output of the "T" fitting is routed to each of the collection bottle/breast cup assemblies 29 (FIG. 4) via vacuum tubing 7.

Figure 6:
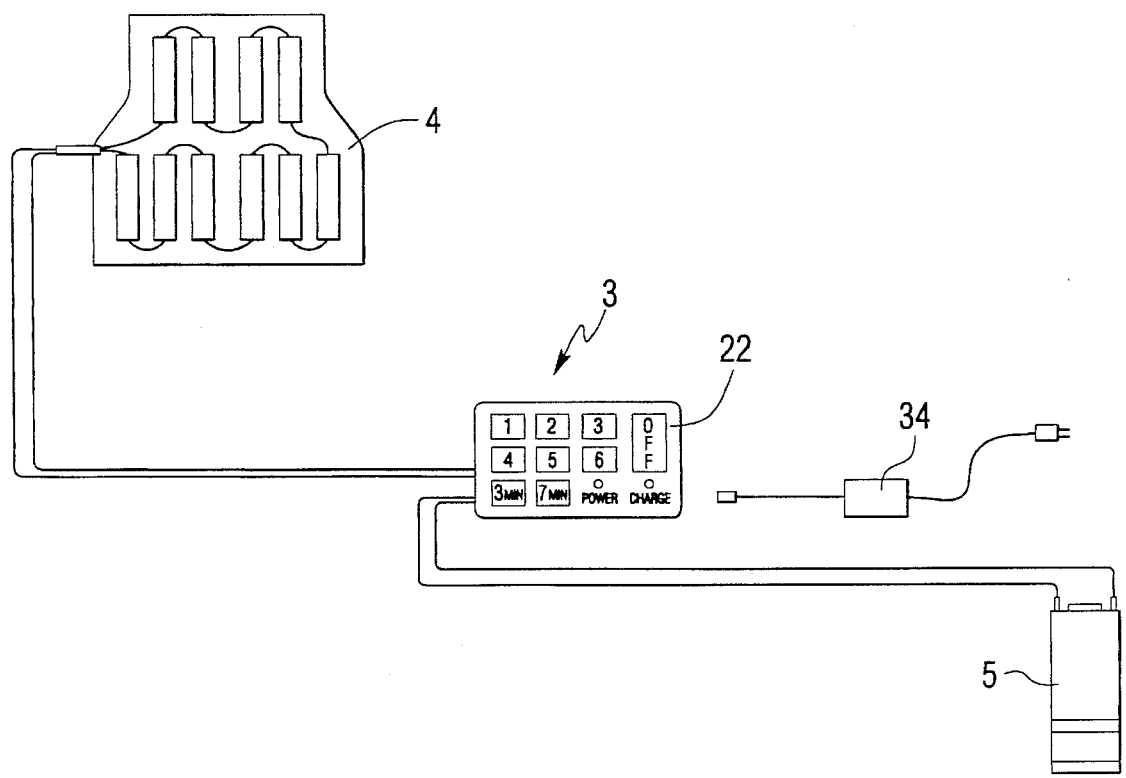
FIG. 6 is a schematic of a motor, controller and power supply for the vested lactation system of FIG. 1.
Figure 7A:
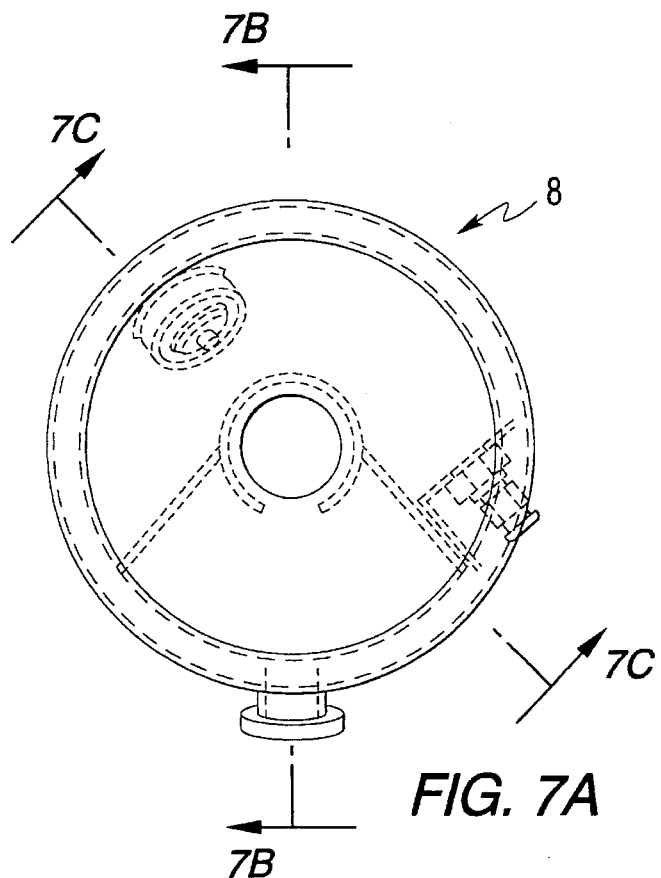
FIG. 7 is a detailed schematic of the breast cup of FIG. 4 and for the vested lactation system of FIG. 1.
Figure 7D:
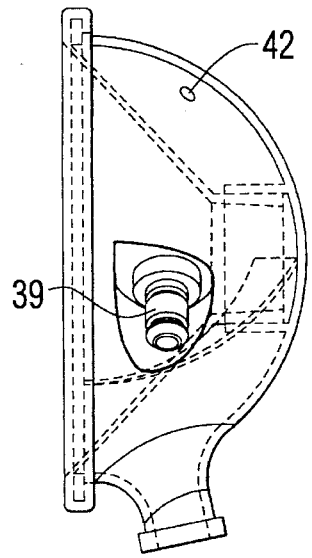
Figure 7B:
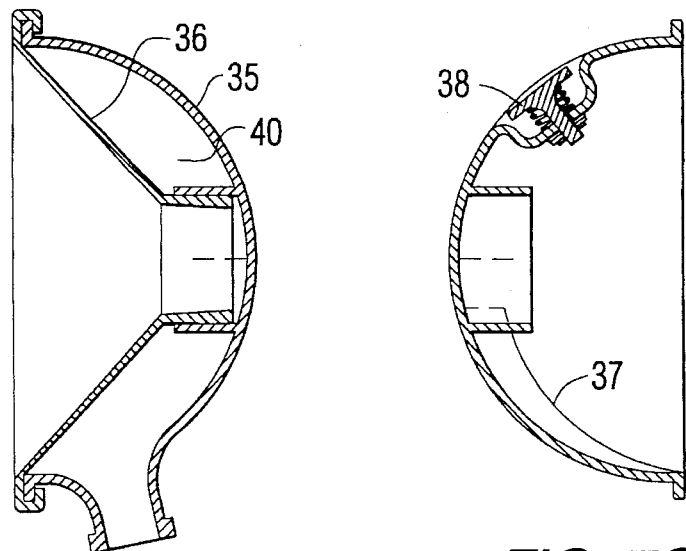
Figure 7C:
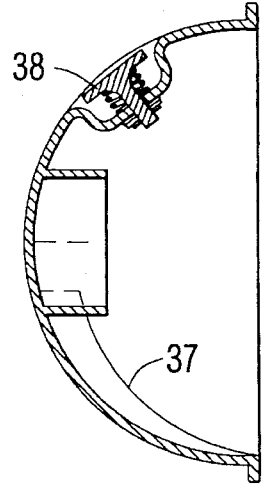
Figure 7E:
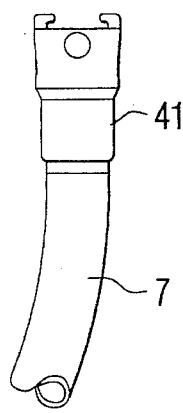

Referring to FIG. 6, the battery pack 4 is the power supply for the direct drive motor 5. The power is routed through the controller 3 to the motor 5. The power output to the motor 5 is regulated as to voltage and duration corresponding to the user's input to the keypad 22. The charger 34 is used to recharge the battery pack 4 and may be used to power the system when batteries are not charged.

FIG. 7 shows the breast cup assembly 8 of FIG. 1 and FIG. 4 in more detail. The outer shell 35 is attached to the flexible annular ring 36. The annular ring 36 forms the seal between the breast and the breast cup assembly 8. Low pressure in the breast cup cavity 40 generated by the vacuum head 6 draws lactate from the breast. Gravity causes the lactate to flow into the collection bottle 10. The baffle 37 halts the accidental flow of lactate into the vacuum tubing 7. The vacuum release valve 38 allows the user to quickly break the vacuum seal between the breast cup assembly 8 and the breast. The vacuum tubing 7 connects to the interface nipple 39 via a quick release fitting 41, which when disconnected allows user to stop the vacuum going to one of the breast cup assemblies. The quick release fitting 41 has a shutoff valve contained within it. This disconnected configuration allows for pumping of a single breast. A vacuum pressure release opening 42 on the outer shell 35 allows accelerated release of vacuum between vacuum pumping cycles.

While I have shown and described an embodiment in accordance with the present invention, it is to be understood that the same is not limited thereto but is susceptible to numerous changes and modifications as known to a person skilled in the art, and I therefore do not wish to be limited to the details shown and described herein but intend to cover all such changes and modifications as are obvious to one of ordinary skill in the art.

What is claimed:

1. A lactation system, comprising:

a vest worn by a user allowing hands free operation and full mobility of said user during lactation, said vest being adjustable to fit various user shapes and sizes, and being configured for attachment of all required hardware to said vest;

a vacuum system having a vacuum source;

a lactate store;

a breast cup assembly containing two breast cups disposed within said vest for interface of a breast and said vacuum system, and being comprised of a rigid outer shell and a flexible inner annular ring dimensionally configured to receive a breast, and having an element for quickly increasing pressure within a breast cup to atmospheric pressure, a vacuum source attachment arrangement for attaching and disconnecting said vacuum source to said breast cup, said breast cup assembly being configured to prevent flow of lactate into a vacuum line of said vacuum system, and a connector for flexibly connecting said lactate store to said breast cup;

said vacuum system being operative to impart a negative pressure to said breast cup and thereby draw a breast into an opening of said flexible inner annular ring of said breast cup to extract lactate;

said lactate store storing lactate during system operation;

a control unit which is coupled to said vacuum system and controls vacuum magnitude and cycle frequency of said vacuum system; and a power unit which is coupled to said vacuum system and said control unit and supplies power to said vacuum system and said control unit.

2. A lactation system according to claim 1, further comprising a rigid, open dome shaped outer shell removably disposed within said vest, said open dome shaped outer shell having a tubular port extending downward from a lower portion of said open dome shaped outer shell, allowing a flow path of lactate, and wherein said flexible annular ring, which is dimensionally configured to receive a breast, is removably attached to an opening of said open dome shaped outer shell, and wherein said element comprises a quick release vacuum fitting affixed to said open dome shaped outer shell to quickly increase pressure of said breast cup to near atmospheric pressure and further including a baffle mounted to a concave side of said open dome shaped outer shell for preventing the flow of extracted lactate into said vacuum line of said vacuum system.

3. A lactation system according to claim 2, wherein said lactate store comprises a lactate collection bottle and further comprising a flexible bellows removably attached to a tubular port of said breast cup extending downward from a lower portion of said tubular port and attaching to an opening of said lactate collection bottle, said flexible bellows allowing a variation of breast cup positions and ease of disassembly for cleaning, said flexible bellows being formed of an elastomeric material in the form of an accordion-configured tube.

4. A lactation system according to claim 3, wherein said lactate collection bottle is formed of a plastic material, with a round opening at a top portion thereof, allowing flow of lactate into said lactate collection bottle, said lactate collection bottle having an interface to said bellows at said opening, said lactate collection bottle having a thickness less than a width thereof, to keep said lactate collection bottle from protruding from under a breast.

5. A lactation system according to claim 2, further including an automatic vacuum cutoff, which is operative, such that, when a vacuum line is removed from said quick release vacuum fitting, there is no appreciable vacuum loss, and wherein said automatic vacuum cutoff comprises an automatic valve incorporated into one of said vacuum line and said quick release vacuum fitting.

6. A lactation system according to claim 2, wherein said baffle comprises a flexible membrane transversely attached to a lower concave side of said outer shell, thereby preventing flow of extracted lactate into said vacuum line system.

7. A lactation system, according to claim 1, further comprising a lightweight housing for containment of said control unit, said housing having openings to allow access to said control unit, said control unit including a microprocessor which is programmed for several vacuum magnitudes and cycle frequency combinations, and wherein vacuum magnitude and cycle frequency options include low, medium and high settings, and wherein a duration of a vacuum cycle may be set to a variety of time settings, a keypad for user input affixed within said housing and accessible to said user, a fuse removably attached within said housing for protection of said user and internal circuitry of said control unit, a battery charging circuit allowing recharging of a power supply of said power unit without removal of said power supply from said vest, and a battery recharge jack allowing connection of an external power supply for recharging said power supply without removal of said power supply from said vest.

8. A lactation system according to claim 1, further comprising a system of vacuum tubing fluidly connecting a vacuum pump of said vacuum system to each breast cup of said breast cup assembly, said system of vacuum tubing being disposed within said vest as an integral part of said vest, and wherein said system of vacuum tubing is routed, as a single line, from a high volume vacuum pump head of said vacuum pump to a vacuum "T" fitting, with an output of said "T" fitting being coupled to two vacuum lines, each vacuum line being routed to a quick release vacuum fitting on each breast cup.

9. A lactation system according to claim 8, further comprising a battery operated electric motor, a high volume vacuum pump head and a noise suppression system, said motor, pump head and noise suppression system being disposed within a pocket formed on a front side of said vest, said pump head being directly attached to and driven by said motor, and wherein said vacuum tubing is fluidly attached to a vacuum port of said pump head.

10. A lactation system according to claim 9, further comprising a rechargeable battery pack for supplying power to said electric motor, said battery pack being comprised of electrically interconnected rechargeable batteries that are physically distributed within a flexible housing, said flexible housing being disposed within a pocket formed on said vest, said flexible housing being of a form such that said batteries are of minimum discomfort to said user.

11. A lactation system according to claim 10, wherein said housing is disposed within a pocket formed on a backside of said vest, said battery housing being made of an elastomeric material extending approximately from a waistline of said user vertically to below shoulder blades of said user.

12. A lactation system according to claim 1, wherein said element includes a vacuum pressure release opening contained within said vacuum system to allow accelerated release of vacuum between vacuum pumping cycles.

\* \* \* \* \*